United States Patent
Yaguchi

(10) Patent No.: US 6,290,828 B1
(45) Date of Patent: Sep. 18, 2001

(54) CIRCUIT FOR MEASURING OXYGEN CONCENTRATION

(75) Inventor: Osamu Yaguchi, Kashiwazaki (JP)

(73) Assignee: Kabushiki Kaisha Riken, Tokyo (JP)

( * ) Notice: Subject to any disclaimer, the term of this patent is extended or adjusted under 35 U.S.C. 154(b) by 0 days.

(21) Appl. No.: 09/227,103

(22) Filed: Jan. 7, 1999

(30) Foreign Application Priority Data

Jan. 9, 1998 (JP) .................................................. 10-015036

(51) Int. Cl.⁷ .................................................. G01N 27/41
(52) U.S. Cl. .......................................... 204/425; 204/406
(58) Field of Search .................................. 204/406, 424, 204/425, 426, 427, 428, 429

(56) References Cited

U.S. PATENT DOCUMENTS

| | | | |
|---|---|---|---|
| 4,359,030 | * | 11/1982 | Sone et al. ........................... 204/406 |
| 4,664,773 | * | 5/1987 | Suzuki et al. ......................... 204/406 |
| 4,799,018 | * | 1/1989 | Ichikawa et al. ..................... 204/406 |
| 5,423,963 | * | 6/1995 | Fletcher et al. ....................... 204/406 |

* cited by examiner

Primary Examiner—Robert J. Warden, Sr.
Assistant Examiner—Kaj K. Olsen
(74) Attorney, Agent, or Firm—Hopgood, Calimafde Judlowe & Modolino LLP

(57) ABSTRACT

A rush current to an oxygen sensor is restricted to very small to secure the high reliability of oxygen sensor.

A non-inverting input of an amplifier 30 is grounded. A resistor 31 is connected between an inverting input and an output of said amplifier 30. A limited electric current type oxygen sensor 34 is connected between said inverting input of said amplifier and a reference power supply 33.

1 Claim, 3 Drawing Sheets

CIRCUIT FOR MEASURING OXYGEN CONCENTRATION

FIELD OF THE INVENTION

The present invention relates to a circuit in which a limited electric current of a limited electric current type oxygen sensor is measured to decide an oxygen concentration.

BACKGROUND OF THE INVENTION

The limited electric current type oxygen sensor is a sensor which can widely detect an oxygen concentration by using an oxygen ion pump function of a zirconia solid electrolyte system. Its basic principle is shown in FIG. 1. When a cell voltage is applied between electrodes sandwiching the zirconia solid electrolyte, oxygen molecules supplied to a negative electrode on a detective gas side through a diffusion resistance layer become oxygen ions on the negative electrode surface, and an electric current appears by movement of the oxygen ions inside the solid electrolyte from cathode to anode. This electric current value is limited by quantity of oxygen molecules diffused in the diffusion resistance layer.

Therefore, because the quantity of oxygen molecules diffused in the diffusion resistance layer is proportional to the oxygen concentration of the detective gas, the relationship between applied cell voltage and electric current shows a limited electric current characteristic in which every output currents are saturated by constant values as shown in FIG. 2, when the oxygen concentration is regulated. These saturated current values become values each proportional to oxygen concentrations in the detective gas, and oxygen concentrations can be detected by reading these electric current values.

In the conventional circuit for measuring oxygen concentration generally used, a constant voltage is supplied to an output of a grounded limited electric current type oxygen sensor through a load resistor and an electric current value flown through an oxygen sensor is detected as a voltage drop in the load resistor to obtain its oxygen concentration. This circuit is found to be difficult to detect accurate oxygen concentration because an output voltage or a cell voltage is changed by changing an oxygen concentration.

FIG. 3 shows a concentration detecting circuit of oxygen sensor disclosed in JP-A-9-166,573 official gazette. In the drawing, a variable reference voltage source 12 is connected between a non-inverting input of an operational amplifier 10 and ground. Moreover, an oxygen sensor 14 is connected between its inverting input and ground, and a detection resistor 16 is connected between the inverting input and its output.

Therefore, a constant cell voltage is intend to be applied the oxygen sensor 14 to obtain its electric current value due to the voltage drop of the detection resistor 16. However, to obtain the voltage drop corresponding to the oxygen concentration, a subtracter subtracting the cell voltage of oxygen sensor from the output voltage of the operational amplifier 10 is necessary.

The subtracter disclosed in this laid-open official gazette seems to be incomplete invention because it discloses the unnecessary resistor 20 connected to a non-inverting input of a differential amplifier 18 while it does not provide any feedback resistor between an output and an inverting input of the differential amplifier 18. The addition of this differential amplifier 18 causes measurement errors increase by a resistance value variation due to the deviation of the offset or the temperature change and aged deterioration. Moreover, components of the detection circuit are increased, and it is needless to say that their costs are raised.

Furthermore, a rush current sometimes flows to the oxygen sensor when turning on or off a power supply of the detection circuit is repeated. The higher the rush current is, the longer a recovery time of the sensor to a normal condition is. The oxygen sensor is also likely to be broken down in rarely by the rush current. Therefore, in FIG. 3, there is a certain limit to increase the value of the detection resistor 16 in view of the existence of the differential amplifier 18. In other words, the smaller this resistance value is, the more accurate the output of the differential amplifier is but the more difficult a protection against the rush current of the oxygen sensor is.

SUMMARY OF THE INVENTION

Accordingly, it is an object of the invention to provide a circuit for measuring oxygen concentration having extremely reduced measurement error, improved reliability and low cost.

The circuit for measuring oxygen concentration according to the invention is characterized in that a non-inverting input of an amplifier is grounded; a resistor is connected between an inverting input and an output of said amplifier; and a limited electric current type oxygen sensor is connected between said inverting input of said amplifier and a reference power supply.

In this amplifier, the voltage of the inverting input is operated to be always identical to the ground electric potential. Then, the cell voltage applied to the oxygen sensor is always constant even if the limited electric current value is changed by oxygen concentration. Because an input impedance of the operational amplifier is very high, the limited electric current flown through the oxygen sensor flows almost all through the resistor. Therefore, the output voltage of the operational amplifier accurately corresponds to the limited electric current value of oxygen sensor (oxygen concentration).

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENT

Figure 1:
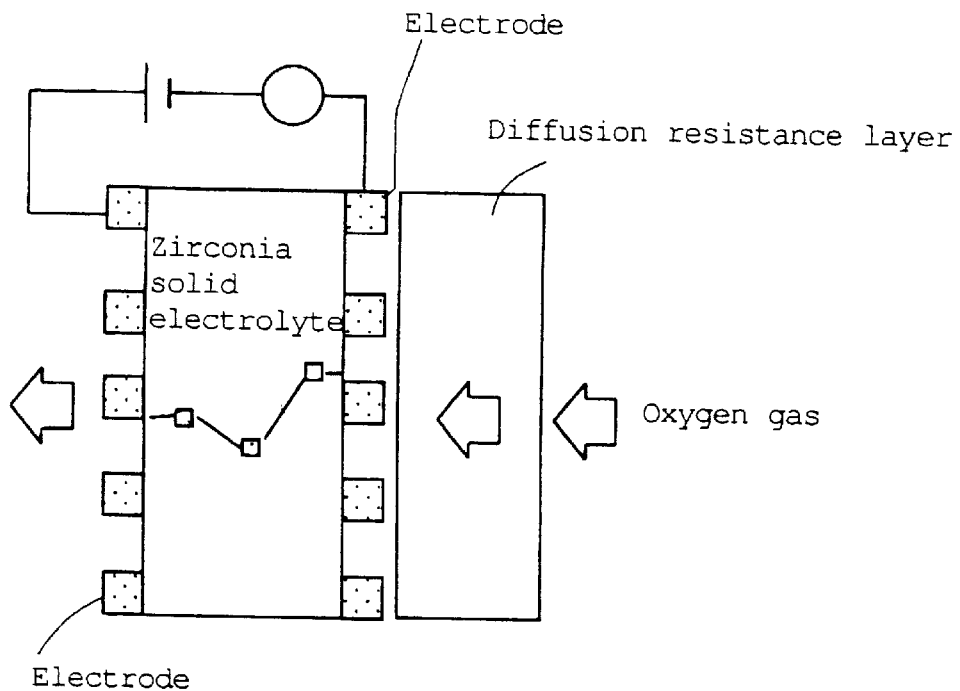
FIG. 1 shows basic principle of the limited electric current type oxygen sensor.
Figure 2:
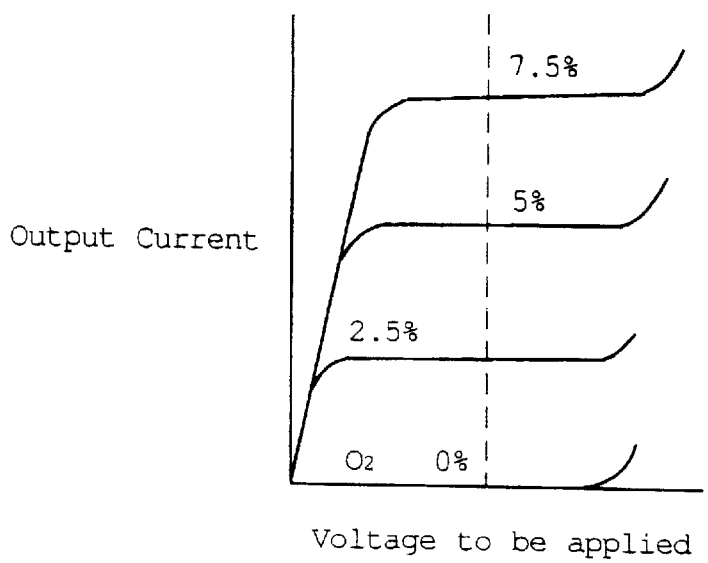
FIG. 2 shows output current characteristics of the limited electric current type oxygen sensor.
Figure 3:
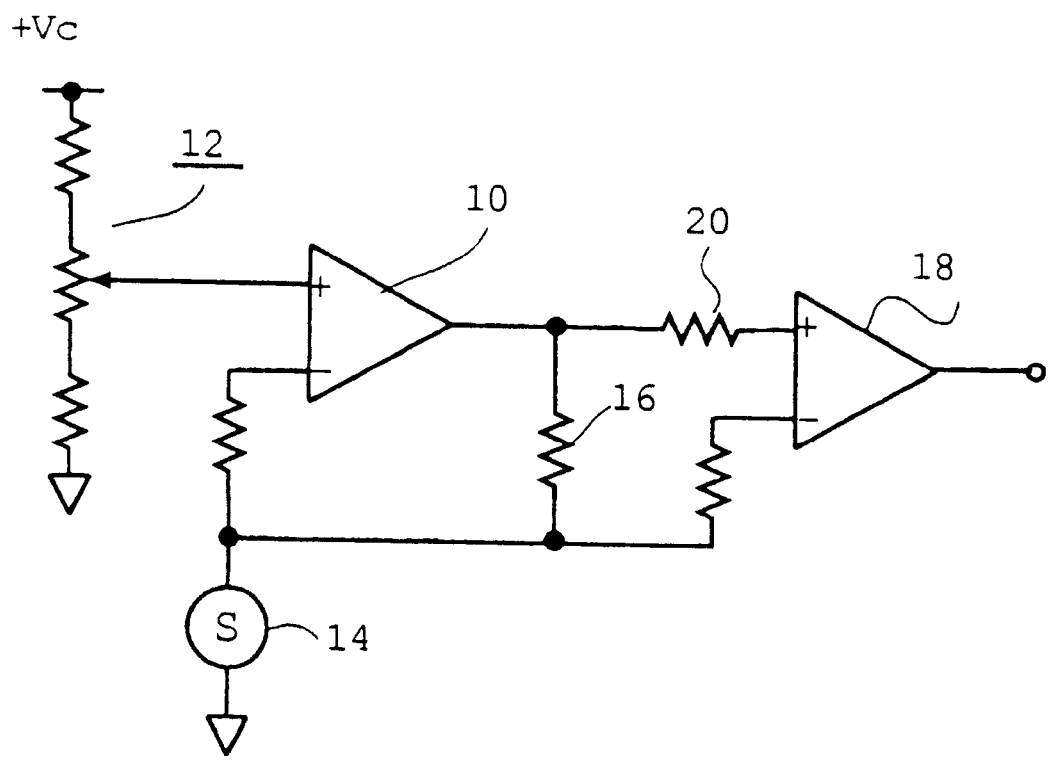
FIG. 3 is a concentration detecting circuit diagram of oxygen sensor of JP-A-9-166,573 official gazette.
Figure 4:
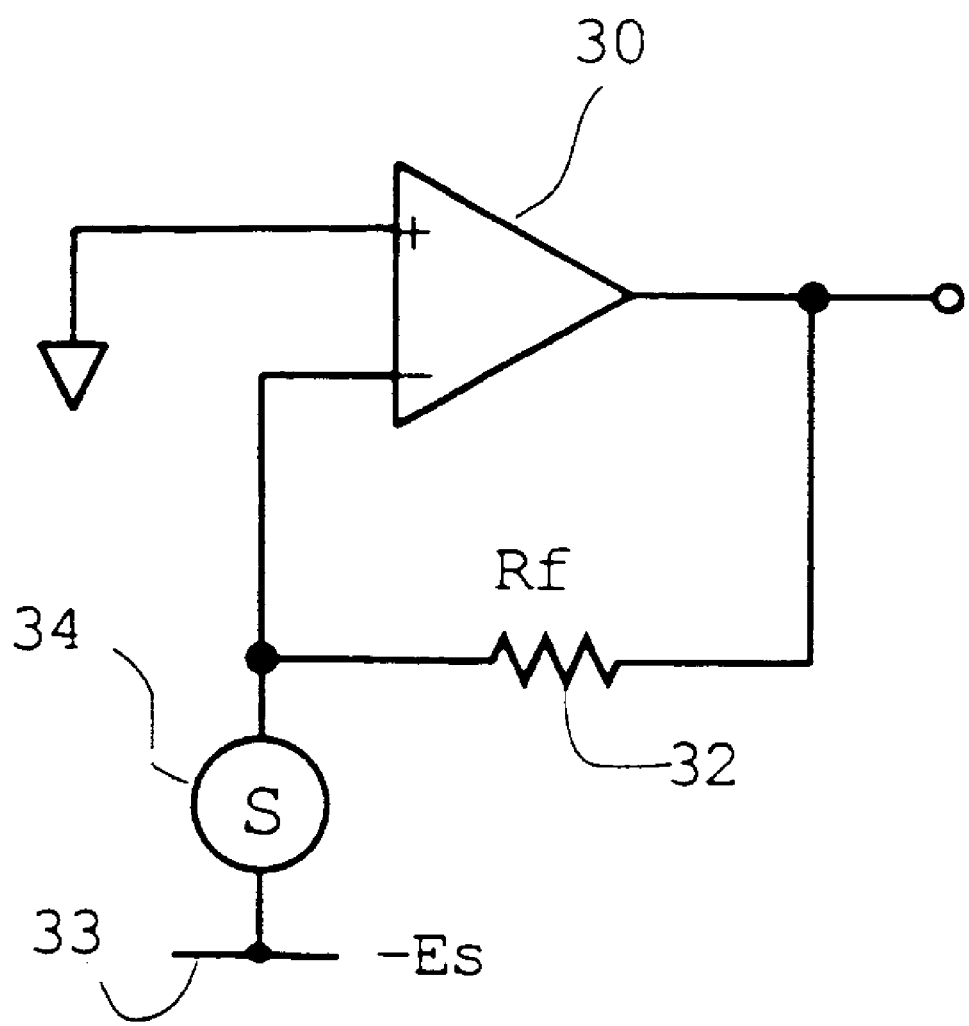
FIG. 4 is a circuit diagram showing an embodiment of circuit for measuring oxygen concentration according to the invention.

Referring now to FIG. 4, a circuit diagram showing an embodiment of circuit for measuring oxygen concentration according to the invention is shown. In FIG. 4, in an amplifier 30 usually used a generally purposed operational amplifier, its non-inverting input is grounded, a detection resistor 32 is connected between its inverting input and its output, and a limited electric current type oxygen sensor 34 is connected between the inverting input and a negative reference power supply 33. As is conventional, the amplifier also has positive and negative power terminals (not shown) connected to positive and negative power supply lines (not shown), respectively.

The basic action of this circuit is as mentioned the above. A predetermined cell voltage Es is applied to an oxygen sensor 34. Moreover, because the non-inverting input of the operational amplifier 30 is grounded, a detected electric current flows through the resistor 32 and oxygen sensor 34 so that the voltage of its inverting input is equal to 0 volt. Therefore, the cell voltage is never changed even if the limited electric current value i of oxygen sensor 34 (oxygen concentration) is changed.

As the result, the output voltage e0 (e0=Rf×i) of the operational amplifier 30 is identical to the value accurately corresponding to the limited electric current value i of oxygen sensor 34.

(i=e0/Rf)

The higher the resistance value Rf of the negative feedback resistor 32 is, the higher the sensitivity of the measuring circuit is and simultaneously the higher reliability of oxygen sensor 34 can be secured because the rush current flown through the oxygen sensor 34 can be restricted to very small.

In the embodiment, Rf=100 kilo ohms, line voltages are set up in ±15 volts, respectively. Therefore, the electric current more than 15 volts/100 kilo-ohms, or 150 $\mu$A is not flown through the oxygen sensor 34.

In FIG. 4, same functions can be obtained even if positive and negative electrodes of oxygen sensor 34 are reversed to apply a reversed positive +Es as the cell voltage. In this case, the output voltage occurs at the negative side against the limited electric current value of oxygen sensor S or 34.

As described the above, in the circuit for measuring oxygen concentration of this invention, an applied cell voltage is constant, and its output voltage is corresponded to the limited electric current value of oxygen sensor (oxygen concentration) regardless of the limited electric current value of the oxygen sensor. Therefore, the oxygen concentration can be measured precisely, and an oxygen concentration measurement device can be constructed with the low cost comparatively.

Because the rush current to oxygen sensor can be restricted to very small, the high reliability of oxygen sensor can be secured without decreasing response rate.

Alternatively, a unitary power supply may be utilized instead of two positive and negative power supplies. In this case, a non-inverting input of said amplifier is connected to a middle point of divider resistors, or a junction of upper and lower resistors. The upper end of the upper resistor and a positive power terminal of the amplifier are connected to a positive power line of the unitary power supply. The lower end of the lower resistor and a negative power terminal of the amplifier are connected to a ground line of the unitary power supply.

The foregoing disclosure and description of the invention are illustrative and explanatory thereof, and various changes in the size, shape, materials, components, circuit elements, wiring connections and contacts, as well as in the details of the illustrated circuit and construction and method of operation may be made without departing from the spirit of the invention.

What is claimed is:

1. A circuit for measuring oxygen concentration in a detective gas, comprising:
    an amplifier having positive and negative power terminals connected to positive and negative power supply lines, respectively;
    a resistor connected between an inverting input and an output of said amplifier; and
    a limited electric current type oxygen sensor connected between said inverting input of said amplifier and a reference power supply, and wherein a non-inverting input of said amplifier connected to ground.

* * * * *